US00PP25218P3

(12) United States Plant Patent
Hill

(10) Patent No.: US PP25,218 P3
(45) Date of Patent: Jan. 6, 2015

(54) ***VRIESEA* PLANT NAMED 'V821-1'**

(50) Latin Name: ***Vriesea* hybrid**
Varietal Denomination: V821-1

(71) Applicant: Herb Hill, Lithia, FL (US)

(72) Inventor: Herb Hill, Lithia, FL (US)

( * ) Notice: Subject to any disclaimer, the term of this patent is extended or adjusted under 35 U.S.C. 154(b) by 113 days.

(21) Appl. No.: 13/815,138

(22) Filed: Jan. 31, 2013

(65) Prior Publication Data

US 2014/0215667 P1 Jul. 31, 2014

(51) Int. Cl.
*A01H 5/00* (2006.01)

(52) U.S. Cl.
USPC ..... Plt./370

(58) Field of Classification Search
USPC ..... Plt./370
See application file for complete search history.

*Primary Examiner* — Susan McCormick Ewoldt

(57) ABSTRACT

A new and distinct *Vriesea* cultivar named 'V821-1' is disclosed, characterized by dark pink inflorescence, and a unique somewhat striped foliage. The new variety is a *Vriesea*, typically produced as an indoor ornamental plant.

1 Drawing Sheet

Latin name of the genus and species: *Vriesea* hybrid.
Variety denomination: 'V821-1'.

BACKGROUND OF THE INVENTION

The new cultivar is a product of a planned breeding program. The new variety originated from a cross pollination of an, unpatented proprietary *Vriesea* hybrid seed parent referred to as 'V420-5' and the pollen parent, an unpatented, proprietary variety of *Vriesea* hybrid referred to as 'V602-6'. The crossing was made during March of 2002.

The new variety was discovered by the inventor, Herb Hill., a citizen of the United States, in September 2006 in a group of seedlings resulting from the crossing. The new cultivar was found in a research greenhouse in Lithia, Fla.

Asexual reproduction of the new cultivar 'V821-1' was first performed at a commercial laboratory in Florida by tissue culture during March of 2007. During this time, no access to plants was available to the public. The first public access to the variety occurred August 2012. Subsequent propagation by tissue culture has shown that the unique features of this cultivar are stable and reproduced true to type.

SUMMARY OF THE INVENTION

The cultivar 'V821-1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'V821-1.' These characteristics in combination distinguish 'V821-1' as a new and distinct *Vriesea* cultivar:

1. Unique dark pink inflorescence color.
2. Unusual leaf color with striping.

PARENT COMPARISON

Plants of the new cultivar 'V821-1' are similar to the unpatented seed parent in most horticultural characteristics. The new variety however differs in the following characteristic:

1. 'V821-1' has a dark pink inflorescence whereas the seed parent has an orange inflorescence.

Plants of the new cultivar 'V821-1' are similar to the pollen parent in most horticultural characteristics. The new variety however differs in the following characteristic:

1. 'V821-1' has a dark pink inflorescence whereas the pollen parent has a pink and orange inflorescence.

COMMERCIAL COMPARISON

'V821-1' can be compared to the unpatented commercial variety of *Vriesea* known as 'Madonna'. Plants of *Vriesea* 'Madonna' are similar to plants of 'V821-1' in most horticultural characteristics. However 'V821-1' differs from 'Class' in the following characteristics:

1. 'V821-1' has a different plant shape than 'Madonna'.
2. 'V821-1' produces a dark pink inflorescence, whereas 'Madonna' produces and white and pink inflorescence.
3. Plants of 'V821-1' produce leaves that have a striping pattern, whereas leaves of 'Madonna' are solid.

BRIEF DESCRIPTION OF THE PHOTOGRAPH

The accompanying photograph in FIG. 1 illustrates in full color a typical plant of 'V821-1' grown in a greenhouse in De Kwakel, the Netherlands. This plant is approximately 20 months old, shown in an 12 cm. pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'V821-1' plants grown in a climate controlled greenhouse in De Kwakel, the Netherlands. Temperatures ranged from 18° C. to 22° C. at night to 20° C. to 28° C. during the day. No artificial light, photoperiodic or chemical treatments were given to the plants. Measurements and numerical values represent averages of typical plant types.

Botanical classification: *Vriesea* hybrid 'V821-1'.

PROPAGATION

Type of propagation typically used: Tissue culture.

Time to initiate roots: About 15 days at approximately 20° C.

Time to produce a rooted cutting/liner: About 180 days at approximately 22° C.

Root description: Moderately dense, moderately branched, fine, fibrous, not fleshy, colored near RHS Greyed-Orange 163D.

PLANT

Growth habit: Main rosette with inflorescence growing from the centre;

*Overall plant-shape*.—Broad ovate.

Height:

*Approximately*.—32.5 cm.

Plant spread:

*Approximately*.—35.6 cm.

Normal pot size: 12 cm pot.

Growth rate: Moderate.

Branching characteristics: Monopodial, leaves form a basal rosette, inflorescence grows from the center of the rosette. No stem present.

Number of leaves per scape:

*Average*.—32.

FOLIAGE

Leaf:

*Arrangement*.—Rosulate (in a basal rosette).

*Average length*.—Approximately 21.1 cm.

*Average width*.—Approximately 4.8 cm.

*Shape of blade*.—Ligulate.

*Aspect*.—Leaves in an average angle of 50° to vertical (=0°).

*Apex*.—Abruptly acute, tip pointed downward 45° (horizontal=0°) .

*Base*.—Decurrent. Sheath length: Average 5.5 cm. Sheath width: Average 8.0 cm. Sheath color: Both sides yellow-green; near RHS 146C, tinged greyed-purple; near RHS N187B to N187C.

*Margin*.—Entire.

*Texture of top surface*.—Smooth, very glossy.

*Texture of bottom surface*.—Smooth, glossy.

*Color*.—Young foliage upper side: Green to yellow-green; in between near RHS 143C and 144A, irregularly axially striped green; near RHS 143A. Young foliage under side: Green to yellow-green; in between near RHS 143C and 144A, irregularly axially striped green; near RHS 143A. Mature foliage upper side: Green; in between near RHS N137A and 143A, but darker, irregularly axially striped yellow-green; near RHS 147A but darker. Mature foliage under side: Yellow-green; near RHS 146B, irregularly axially striped yellow-green; near RHS 147A.

*Venation*.—Type: Parallel. Venation coloration: Indistinguishable from leaf blade.

Petiole: No petioles present, leaves sheathing.

INFLORESCENCE

General description: Scape growing from the center of the basal rosette, inflorescence branched into a paniculate shape; only bracts visible, individual flowers not visible but fully enclosed by bracts.

*Inflorescence height, excluding scape*.—Approximately 24.1 cm.

*Inflorescence width*.—Approximately 12.8 cm.

Scape:

*Length*.—Approximately 17.9 cm.

*Width*.—Approximately 0.7 cm.

*Aspect*.—Approximately 90° angle to rosette (=0°).

*Strength*.—Strong.

*Color*.—Greyed-orange; near RHS 172A.

Bracts:

*Scape/lowermost bracts*.—Shape: Broad ovate. Length: Approximately 1.6 cm, excluding sheath. Width: Approximately 1.5 cm. Quantity: Average 8. Tip: Broad apiculate. Base: Sheathing. Sheath length: Approximately 3.9 cm. Sheath width: Approximately 2.6 cm. Sheath color: Yellow-green; near RHS 148D, tinged greyed-green; 196A. Margin: Entire. Color Upperside: Green; near RHS 143A, yellow-green towards the base; near RHS 147D. Color Underside: Yellow-green; near 144A, lighter towards the base; near RHS 144C.

*Terminal bracts*.—Shape: Ovate, folded (flattened). Length: Approximately 2.1 cm, excluding sheath. Width: Approximately 2.2 cm; however, bracts are folded, so effectively it is two times 1.1 cm. Quantity: Average 61. Tip: Apiculate. Base: Sheathing. Sheath length: Approximately 3.5 cm. Sheath width: Approximately 2.8 cm; however, bracts are folded, so effective it is two times 1.4 cm. Sheath color: Red; near RHS 53D. Margin: Entire. Coloration Terminal Bracts: Upperside: Red; near RHS 53B. Underside: Red; near RHS 53B.

FLOWER

Flowering characteristics: Individual flowers fully enclosed by the bracts and therefore not visible from outside; each bract encloses one individual flower.

Days to flowering (better is: to commercial plant) from tissue culture: 2 to 2.5 years.

Inflorescence and flower type and habit: Inflorescence paniculate, individual flower single.

Flower longevity on plant:

*Average*.—3 months.

Quantity of buds and flowers per plant:

*Average*.—61.

Persistent or self-cleaning: Persistent.

Bud:

*Shape*.—Lanceolate.

*Length*.—Average: 1.3 cm.

*Diameter*.—Average: 0.3 cm.

*Color*.—Yellow-green; near RHS 145B, base lighter, near RHS 150D.

Flower size:

*Diameter*.—Average: 0.4 cm.

*Depth*.—Average: 2.1 cm.

Petals:
*Quantity*.—Average: 3.
*Arrangement*.—Rotate, fused.
*Length*.—Average: 1.1 cm.
*Width*.—Average: 0.3 cm.
*Shape*.—Lanceolate, fused.
*Apex*.—Acute.
*Base*.—Cuneate, fused.
*Margin*.—Fused.
*Texture, upper and lower surfaces*.—Smooth, slightly glossy.
*Color*.—When opening, upper surface: White; near RHS 155A, tip green-yellow; near 1B. When opening, lower surface: White; near RHS 155A, tip green-yellow; near 1B. Fully opened, upper surface: White; near RHS 155A, tip green-yellow; near 1B. Fully opened, lower surface: White; near RHS 155A, tip green-yellow; near 1B.

Staminoides: No staminodes present.

Sepals:
*Quantity*.—Average: 3.
*Length*.—Average: 2.1 cm.
*Width*.—Average: 0.4 cm.
*Shape* (*overall*).—Lanceolate. Apex: Acute. Base: Cuneate, fused.
*Margin*.—Entire.
*Color*.—Yellow-green; near RHS 145C, darker towards the top; 151B.

Peduncles:
*Length*.—Average: 6.1 cm.
*Diameter*.—Average: 0.5 cm.
*Angle*.—About 40° to the lateral branch.
*Strength*.—Strong.
*Texture*.—Smooth, glossy.
*Color*.—Yellow-green; near RHS 144B to 144C.

Fragrance:

REPRODUCTIVE ORGANS

Stamens:
*Number*.—Average: 6.

Anthers:
*Shape*.—Narrow oblong.
*Length*.—Approximately 0.6 cm.
*Color*.—Yellow; near RHS 8B.
*Pollen*.—No pollen detected.

Pistil:
*Number*.—Average: 3.
*Length*.—Average: 0.4 cm.
*Style*.—Length: Average: 0.35 cm. Color: Yellow-white; near RHS 158D.
*Stigma*.—Shape: Club-shaped. Color: Yellow:green; near RHS 151C. Ovary Color: Yellow-white; near RHS 158D.

OTHER CHARACTERISTICS

Disease resistance: Neither resistance nor susceptibility to the normal diseases and pests of *Vriesea* has been observed.

Drought tolerance and cold tolerance: Observed to tolerate temperatures to 35° C. without any negative effects. Temperature tolerance above this range has not been observed. Tolerance of cold temperatures has not been observed.

Fruit/seed production: Not observed to date.

What is claimed is:

1. A new and distinct cultivar of *Vriesea* plant named 'V821-1' as herein illustrated and described.

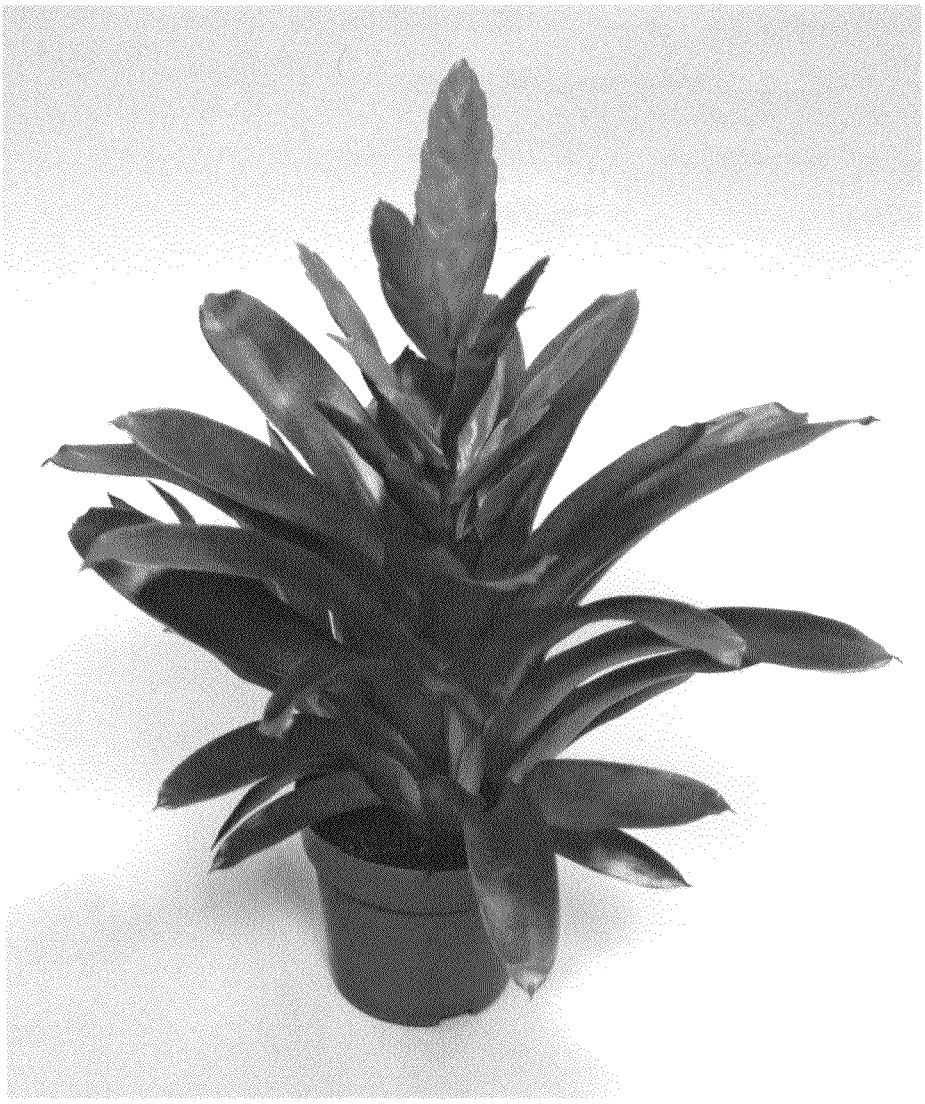

* * * * *